United States Patent [19]

Lenselink

[11] 4,211,674

[45] Jul. 8, 1980

[54] CYCLIC ACETALS AND KETALS AND THEIR USE IN PERFUME COMPOSITIONS

[75] Inventor: Willem Lenselink, Voorthuizen, Netherlands

[73] Assignee: Polak's Frutal Works B.V., Amersfoort, Netherlands

[21] Appl. No.: 23,481

[22] Filed: Mar. 23, 1979

[30] Foreign Application Priority Data

Apr. 10, 1978 [GB] United Kingdom ............... 13958/78

[51] Int. Cl.$^2$ .............................................. C11B 9/00
[52] U.S. Cl. ............................. 252/522 R; 260/340.7; 252/94; 252/174.11; 424/69; 424/358; 424/64; 424/76; 424/70; 106/3; 106/10
[58] Field of Search ....................... 252/522; 260/340.7

[56] References Cited

U.S. PATENT DOCUMENTS

| | | | |
|---|---|---|---|
| 2,993,055 | 7/1961 | Hennis | 252/522 R |
| 3,417,107 | 12/1968 | Chodroff et al. | 252/522 R |
| 3,748,344 | 7/1973 | McCloud et al. | 252/522 R |
| 3,884,841 | 5/1975 | Maessen et al. | 252/522 R |
| 4,010,286 | 3/1977 | Hall | 252/522 R |
| 4,014,905 | 3/1977 | Skorianetz et al. | 252/522 R |
| 4,113,664 | 9/1978 | Conrad et al. | 252/522 R |
| 4,120,830 | 10/1978 | Reuold | 252/522 R |
| 4,136,252 | 1/1979 | Capozza | 260/340.7 |
| 4,146,506 | 3/1979 | Bruns | 260/340.7 |

OTHER PUBLICATIONS

Chem. Ab. 66:37850r, 1967.

*Primary Examiner*—Veronica O'Keefe
*Attorney, Agent, or Firm*—William S. Alexander

[57] ABSTRACT

Novel tricyclic 1,3-dioxanes based on the skeleton of 1,1-dimethyloctalin or 1,1-dimethyldecalin and their use as perfume components is disclosed.

36 Claims, 1 Drawing Figure

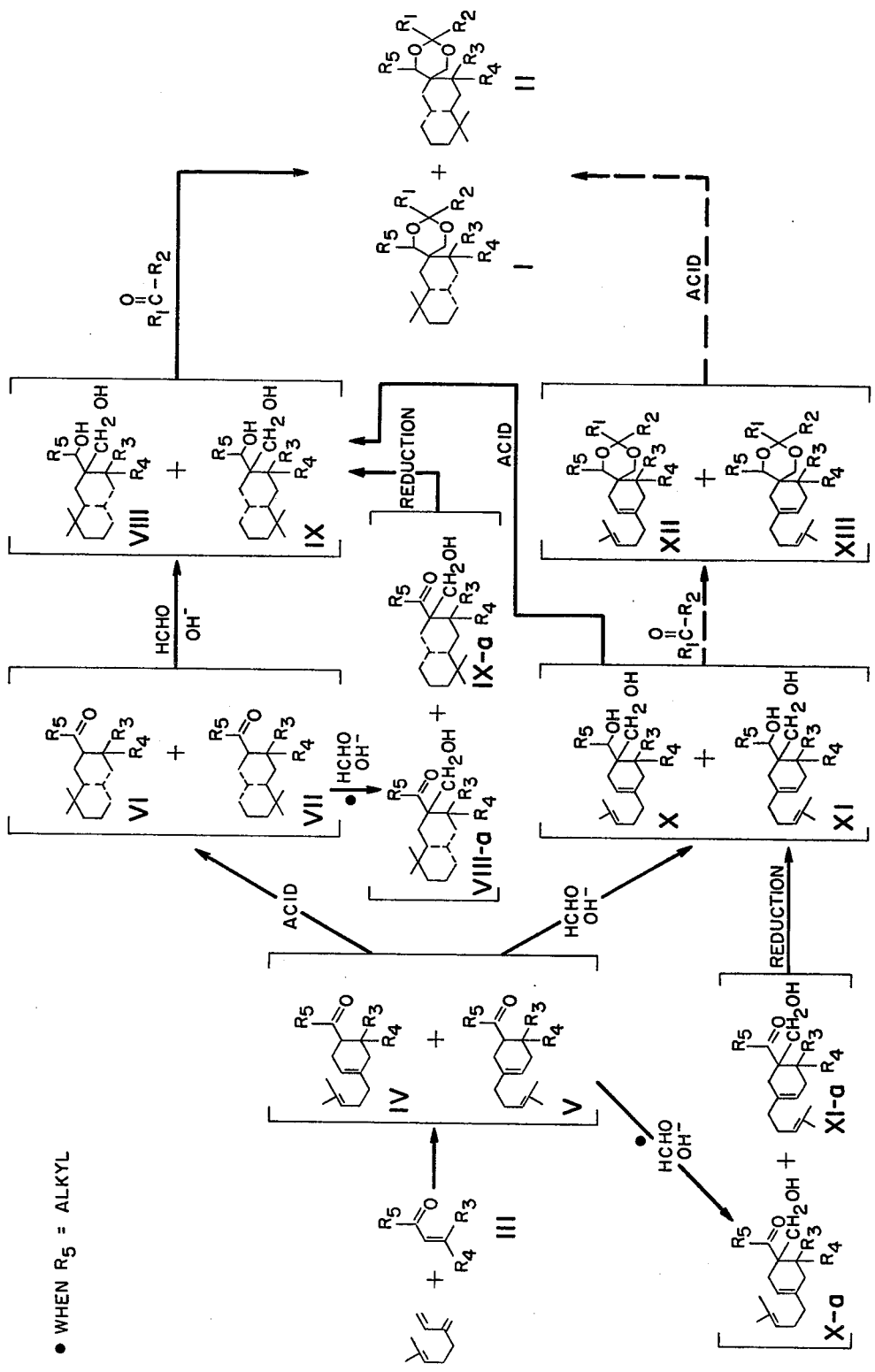

CYCLIC ACETALS AND KETALS AND THEIR USE IN PERFUME COMPOSITIONS

This invention relates to new chemical compounds useful as perfumes or as components of perfumes. Specifically it relates to tricyclic 1,3-dioxanes based on the skeleton of 1,1-dimethyloctalins or 1,1-dimethyldecalins.

In the fragrance industry there is a continuous search for new and useful synthetic fragrance materials. Such materials may offer many advantages over natural products as essential oils and derivatives thereof. For example, synthetic products usually are not so sensitive to factors as availability, price, quality, crop failure, adulteration and organoleptic reproducibility. It is also for these reasons that, especially in the field of the expensive natural oils with highly useful woody odors, for example vetiver oil and sandalwood oil, much effort is being made to find synthetic replacements.

It is the object of the present invention to provide a series of novel 1,3-dioxanes which possess very useful odors of the woody type, which can be obtained from readily available inexpensive starting materials. These novel 1,3-dioxanes are represented by the following general formulae

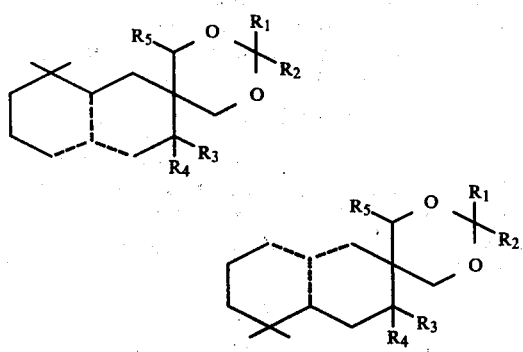

wherein the dotted lines represent carbon-to-carbon double or single bonds with the limitation that only one of the dotted lines can be a double bond and wherein $R_1$ represents hydrogen or a lower alkyl, alkenyl or alkoxy group, $R_2$, $R_3$, $R_4$ and $R_5$ represent hydrogen or a lower alkyl group and the total carbon number of $R_1$, $R_2$, $R_3$, $R_4$ and $R_5$ combined is 6 or less.

The novel compounds can be prepared via a sequence of reactions known to the art. A preferred reaction sequence is set out in the attached drawing, to which reference will now be made.

In the first step of the reaction sequence, myrcene (7-methyl-3-methylene-1,6-octadiene) is reacted via a Diels-Alder condensation with an α,β-unsaturated aldehyde or ketone of formula III to form intermediate oxo compounds IV and V. The Diels-Alder condensation can be conducted thermally, for example, as described by G. Ohloff, Ann. 606 (1957) page 100. It can also be catalyzed by Lewis acids as taught by Wollweber, Diels-Alder Reactions, George Thieme Verlag, Stuttgart (1972), chapter A V, or by Netherlands patent application No. 7,909,668. The reaction modification used for the condensation can influence the ratio of isomers IV and V. Usually, the formation of isomer IV is favored in the Lewis acid catalyzed modification.

Ring closure of the carbon skeleton of the oxo compound to the required octalin configuration can be accomplished by the action of an acidic catalyst as taught by G. Ohloff l.c. The carbon-carbon double bond in the resulting product can be in any of the positions indicated by the dotted lines. Ring closure can be carried out either immediately following oxo compound formation or as the final reaction step.

The oxo compounds IV and V or VI and VII are condensed with formaldehyde and alkali as described by French and Gallagher, J.A.C.S. 64 (1942), page 1497, to form dihydroxy compounds VIII and IX or X and XI. In the case where $R_5$ is an alkyl group, the reaction is preferably stopped at the hydroxyketone stage VIII-a and IX-a or X-a and XI-a, and followed by reduction of the carbonyl oxygen to a hydroxyl group using, e.g., lithium aluminum hydride or sodium borohydride or by catalytic hydrogenation.

The 1,3-dioxane moiety of the novel compounds of the invention preferably is introduced into the dihydroxy compounds of formulae VIII and IX. This can be achieved by known methods, for example as taught by C. A. Buehler and D. E. Pearson, Survey of Organic Synthesis, Wiley Interscience, New York, Chapter 9 of Vol. 1 (1970) and Chapter 9 of Vol. 2 (1977). A preferred method is the acid catalyzed acetalization or ketalization of the dihydroxy-compounds with an aldehyde or ketone of general formula $R_1COR_2$. In case where $R_1$ is an alkoxy group an orthoester is reacted in place of the aldehyde or ketone.

For the preparation of the novel 1,3-dioxanes wherein all the dotted lines in formulae I+II represent carbon-to-carbon single bonds an intermediate hydrogenation step is carried out at a suitable stage in the reaction sequence. For this purpose, the following intermediates advantageously can be hydrogenated by methods known to the art:

(a) The unsaturated bicyclic oxo compounds of formulae VI and VII, for example, as taught G. Ohloff, l.c.;

(b) The unsaturated bicyclic hydroxyketones of formulae VIIIa and IXa;

(c) The unsaturated bicyclic dihydroxy compounds of formulae VIII and IX;

(d) The unsaturated hydroxyketones VIIIa, IXa, simultaneously with hydrogenation to reduce the carbonyl oxygen; and (e) The unsaturated tricyclic 1,3-dioxanes of formulae I and II.

In an alternative route the monocyclic dihydroxy compounds of formulae X and XI can be converted to 1,3-dioxanes XII and XIII prior to the cyclization step. This alternative route is less attractive because of the general instability of the acetals in the acidic medium which is needed for cyclization.

It will be apparent that the novel 1,3-dioxanes can exist in a variety of steroisomeric forms and it is intended that these be included within the structural formulae. Whenever a general structural formula is presented in this text or in the attached claims, it is intended to include all such stereoisomeric forms.

The novel 1,3-dioxanes of the invention exhibit a variety of useful odor nuances. They can be used as fragrances per se or as components of a fragrance composition. The term "fragrance composition" is used to denote a mixture of compounds including, for example, natural oils, synthetic oils, alcohols, aldehydes, ketones, esters, lactones, ethers, hydrocarbons and other classes of chemical compounds which are admixed so that the combined odors of the individual components produce a pleasant or desired fragrance. Such fragrance compositions or the novel compounds of this invention alone can be used in conjunction with carriers, vehicles or solvents containing also, as needed, dispersants, emulsifiers, surface-active agents, aerosol propellants and the like.

In fragrance compositions the individual components contribute their particular olfactory characteristics, but the overall effect of the composition is the sum of the effect of each ingredient. Thus, the 1,3-dioxanes of this invention can be used to alter, enhance, or reinforce the aroma characteristics of the other natural or synthetic materials making up the fragrance composition, for example, by highlighting or moderating the olfactory reaction contributed by another ingredient or combination of ingredients.

The amount of the 1,3-dioxanes of the invention which will be effective depends on many factors including the characteristics of the other ingredients, their amounts and the effects which are desired. It has been found that as little as 0.01% by weight of compounds of this invention can be used to alter the effect of a fragrance composition. The amount employed will depend on considerations of cost, nature of end product, the effect desired in the finished product, and the particular fragrance sought, but will usually not be more than about 50% by weight.

The compounds disclosed herein can be used in a wide variety of applications such as, e.g., detergents and soaps; space deodorants, perfumes, colognes; aftershave lotions; bath preparations such as bath oil and bath salts; hair preparations such as lacquers; brilliantines, pomades and shampoos; cosmetic preparations such as creams, deodorants, hand lotions, and sun screens; powders such as talcs, dusting powders, face powder; as masking agents, e.g., in household products such as bleaches, and in technical products such as shoe polish and automoblie wax.

The following examples illustrate the invention. In all examples, unless otherwise specified, $R_1$, $R_2$, $R_3$, $R_4$ and $R_5$ can be taken to be hydrogen.

EXAMPLE 1

A solution of 65 g. (0.987 mole) 85% potassium hydroxide in 75 ml. water was added in the course of 20 minutes and at a temperature of 70° C. to a mixture of 50 ml. formalin, 125 ml. methanol and 100 g. (0.521 mole) of a 70:30 mixture of compounds of formula VI and VII (Ann. 606, p. 100 (1967)). The reaction mixture was stirred at 70° C. for another hour and then refluxed for 2½ hours.

After cooling the reaction mixture to room temperature, 200 ml. of water was added and the mixture was extracted with ether. The ether extracts were washed with water and with saturated NaCl solution and dried with $Na_2SO_4$. After evaporation of the solvent, distillation yielded 70.5 g. (0.315 mole = 60%) of the compounds of formula VIII and IX, b.p. 150°–158° C. at 0.4 mm Hg, m.p. 80°–83° C.

EXAMPLE 2

A mixture of 20 g. (0.089 mole) of the diol mixture of Example 1, 2.9 g. (0.098 mole) paraformaldehyde, 13.2 g. (0.089 mole) triethylorthoformate and a few crystals of p-toluenesulphonic acid was stirred at 35° C. for 2 hours. Then an additional gram of paraformaldehyde was added and stirring was continued for 1½ hours more. Then the volatile reaction products were distilled off till a bottom temperature of 90° C. was reached. The cooled residue was taken up in ether and washed with saturated $KHCO_3$ solution and saturated NaCl solution and dried with $Na_2SO_4$. After evaporation of the solvent, distillation yielded 17 g. (0.072 mole = 82%) of the Compounds I and II, b.p. 97°–99° C. at 0.2 mm, $n_D^{20} = 1.5072$, with woody, tobacco like odor.

EXAMPLE 3

Analogously to Example 2 a mixture of compounds I and II where $R_1$ is methyl was prepared from the diol of Example 1 and acetaldehyde in 76% yield with quinoline like, woody odor. b.p. 110–112 at 0.5 mm Hg, $n_D^{20} = 1.4998$.

EXAMPLE 4

Analogously to Example 2 a mixture of compounds I and II where $R_1$ and $R_2$ are methyl was prepared from the diol mixture of Example 1 and acetone, in 72% yield with quinoline like, woody odor. b.p. 92°–93° C. at 0.05 mm Hg, $n_D^{20} = 1.4978$.

EXAMPLE 5

Analogously to Example 2 a mixture of compounds I and II where $R_1$ is ethoxy was prepared from the diol mixture of Example 1 without added aldehyde or ketone in 30% yield with metallic, floral odor. b.p. 122°–128° C. at 0.3 mm Hg, $n_D^{20} = 1.4965$.

EXAMPLE 6

Analogously to Example 2 a mixture of compounds I and II where $R_1$ is isopropyl was prepared from the diol mixture of Example 1 and isobutyraldehyde in 77% yield with woody, quinoline like odor. b.p. 121°–123° C. at 0.5 mm Hg, $n_D^{20} = 1.4953$.

EXAMPLE 7

Analogously to Example 1 a mixture of the diols VIII and IX where $R_3$ is methyl was prepared from a mixture of compounds VI and VII ($R_3 = CH_3$) in 50% yield of crystallized material, m.p. = 93°–95° C.

EXAMPLE 8

Analogously to Example 2 a mixture of compounds I and II where $R_3$ is methyl was prepared from the diol mixture of Example 7 and paraformaldehyde in 40% yield with woody, jasminic odor. b.p. 110°–120° C. at 0.5 mm Hg, $n_D^{20} = 1.5027$.

EXAMPLE 9

Analogously to Example 2 a mixture of compounds I and II where $R_1$ and $R_3$ are methyl was prepared from the diol mixture of Example 7 and acetaldehyde in 78% yield with woody, jasminic odor. b.p. 110°–115° C. at 0.4 mm Hg, $n_D^{20} = 1.4980$.

EXAMPLE 10

Analogously to Example 1 a mixture of the diols VIII and IX where $R_3$ is n-propyl was prepared from the compounds VI and VII ($R_3 =$ n-propyl). The crude solid diol mixture was converted in 74% yield to a mixture of the compounds I and II ($R_3 =$ n-propyl) by reaction with paraformaldehyde analogously to Example 2. b.p. 104°–106° C. at 0.1 mm Hg, $n_D^{20} = 1.5020$.

EXAMPLE 11

A mixture of 100 g. (0.485 mole) of the compounds VI and VII where $R_5$ is methyl, 42 g. of 36% formalin (0.520 mole), 150 ml. methanol and 1 ml. 30% sodium hydroxide solution in water was refluxed for 7 hours. Then 50 g. of 36% formalin and 1 ml. of 30% sodium hydroxide were added and the mixture was refluxed for another 6 hours. After cooling to room temperature, water was added and the mixture was extracted with ether. The ether extracts were washed with water and saturated NaCl solution and dried with $Na_2SO_4$. After evaporation of the solvent, distillation yielded 65 g. (0.276 mole=57%) of the compounds VIIIa and IXa where $R_5$ is methyl, b.p. 145°-150° C. at 0.8 mm Hg, $n_D^{20}=1.5140$.

EXAMPLE 12

A solution of 30 g. (0.127 mole) of the compounds VIIIa and IXa of Example 11 in 50 ml. of dry ether was added in the course of 10 minutes to a stirred mixture of 4.3 g. (0.127 mole) of lithium aluminum hydride and 300 ml. of dry ether. The reaction mixture was refluxed for 4 hours and ethyl acetate was added dropwise to neutralize the excess lithium aluminum hydride, followed by water. The mixture was filtered and extracted with ether. The ether extracts were washed with saturated NaCl solution and dried with $Na_2SO_4$. Evaporation of the solvent yielded 32 g. of crude diol mixture which was reacted without further purification with acetaldehyde analogously to Example 2. Obtained was 65% yield of the compounds I and II ($R_2$ and $R_3$ are methyl) with woody odor. b.p. 105°-106° C. at 0.2 mm Hg, $n_D^{22}=1.5002$.

EXAMPLE 13

22.4 g. (0.100 mole) of the diol mixture of Example 1 was hydrogenated with 2.2 g of 10% palladium on carbon in 100 ml. of absolute ethanol in a Parr hydrogenation apparatus at 60° C. After the theoretical hydrogen uptake was reached (8 hours), the mixture was filtered and the solvent was removed by means of a rotary evaporator yielding 22.5 g. of crude saturated diols corresponding to VIII and IX which were reacted without further purification with acetaldehyde analogously to Example 2. Obtained was 75% yield of the saturated dioxanes I and III ($R_2$=$CH_3$) with woody odor. b.p. 104°-106° C. at 0.4 mm hg, $n_D^{20}=1.4874$.

EXAMPLE 14

Analogously to Example 1 a mixture of diols X and XI was prepared from the compounds IV and V (Ann. 606, p. 100 (1957)) in 90% yield, b.p. 146°-149° C. at 0.2 mm Hg, m.p. 38°-39° C.

EXAMPLE 15

Analogously to Example 2 dioxanes XII and XIII were prepared from the diols of Example 14 reaction with paraformaldehyde in 58% yield with woody, metallic odor. b.p. 104°-110° C. at 0.2 mm Hg, $n_D^{20}=1.4955$.

EXAMPLE 16

Analogously to Example 2 dioxanes XII and XIII ($R_1$=$CH_3$) were prepared from the diols of Example 14 by reaction with acetaldehyde in 89% yield with greenish, woody odor. b.p. 114°-120° C. at 0.5 mm Hg, $n_D^{20}=1.4995$.

EXAMPLE 17

22 g. (0.155 mole) Borontrifluoride diethyletherate was added dropwise to a solution of 25 g. (0.112 mole) of the diols prepared in Example 14 in 150 ml. benzene. The temperature rose to 34° C. and the mixture was allowed to cool to room temperature during a 2 hour stirring period. Water was added and the mixture was extracted with ether. The ether extracts were washed neutral with water and dried with $Na_2SO_4$. After evaporation of the solvent, distillation yielded 15 g. (0.067 mole-60%) of the diols VIII and IX of Example 1.

EXAMPLE 18

Analogously to Example 17 to dioxanes of Example 16 were treated with borontrifluoride diethyletherate yielding 30% of the dioxanes I and II ($R_2$=$CH_3$) of Example 3.

EXAMPLE 19

A perfume composition is prepared by admixing the following ingredients:

| | |
|---|---|
| 165 g. | hydroxycitronellal |
| 55 g. | Lyral (IFF) |
| 25 g. | Lilial (Givaudan) |
| 25 g. | Celestolide (IFF) |
| 180 g. | benzyl salicilate |
| 25 g. | phenylethyl phenylacetate |
| 115 g. | phenylethyl alcohol |
| 90 g. | linalool |
| 20 g. | ylang ylang I |
| 45 g. | benzyl acetate |
| 45 g. | rhodinol ex geranium oil |
| 60 g. | γ-methylionone |
| 1 g. | Rose oxyde (Dragoco) |
| 0.5 g. | cis-3-hexenyl acetate |
| 1.5 g. | dihydromyrcenol |
| 0.5 g. | isocyclocitral |
| 0.5 g. | galbanum oil |
| 2 g. | phenylacetaldehyde dimethylacetal |
| 0.5 g. | undecylenic aldehyde |
| 2.5 g. | styrallyl acetate |
| 1 g. | coumarine |
| 120 g. | cyclic acetals prepared according to Example 3 |

The addition of the acetals of Example 3 gives a very clear exalting effect as well as in the top-note as in the body and dry-out of the perfume composition.

EXAMPLE 20

The following formula demonstrates the application of the acetal of Example 9:

| | |
|---|---|
| 100 g. | benzyl salicilate |
| 100 g. | methyl dihydroisojasmonate |
| 85 g. | linalol |
| 50 g. | rhodinol ex geranium-oil |
| 50 g. | linalyl acetate |
| 50 g. | mandarin oil |
| 50 g. | lemon oil |
| 40 g. | patchouli oil |
| 40 g. | vertiveryl acetate |
| 40 g. | alpha-hexylcinnamic aldehyde |
| 40 g. | benzyl acetate |
| 40 g. | musk ketone |
| 30 g. | sandalwood oil |
| 25 g. | cinnamic alcohol |
| 20 g. | ylang-ylang I |
| 20 g. | eugenol |
| 20 g. | cis-hexenyl benzoate |
| 20 g. | Lilial (Givaudan) |
| 20 g. | oakmoss absolute |
| 20 g. | gamma-methylionone |

-continued

| | |
|---|---|
| 10 g. | dihydromyrcenol |
| 10 g. | styrallyl acetate |
| 10 g. | indol - 10%-sol. in isopropyl myristate |
| 5 g. | methylchavicol |
| 5 g. | Jasmonax (PFW) |
| 5 g. | phenylethyl phenylacetate |
| 5 g. | Isodamascone (Dragoco) |
| 5 g. | rose oxide - 10%-sol. in isopropyl myristate |
| 5 g. | undecylenic aldehyde - 10%-sol. in isopropyl myristate |
| 5 g. | methyl actinecarbonate - 10%-sol. in isopropyl myristate |
| 5 g. | iso-eugenol |
| 70 g. | cyclic acetals prepared according to Example 9 |
| 1000 | |

The addition of the acetals of Example 9 gives a distinct and improved effect in the perfume composition.

What I claim and desire to protect by Letters Patent is:

1. A compound selected from the class of compounds having the structural formulae

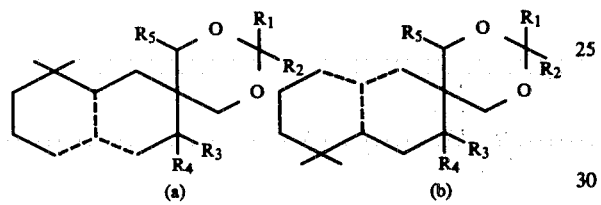

(a)  (b)

wherein $R_1$ is hydrogen or an alkyl, alkenyl or alkoxy group and wherein $R_2$, $R_3$, $R_4$ and $R_5$ are hydrogen or alkyl groups and the total number of carbon atoms of $R_1$, $R_2$, $R_3$, $R_4$ and $R_5$ combined is 6 or less and the dotted lines indicate carbon-to-carbon double or single bonds with the limitation that only one of the dotted lines can be a double bond.

2. A compound of claim 1 having the basic formula

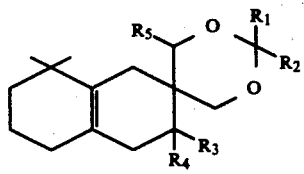

3. A compound of claim 1 having the basic formula

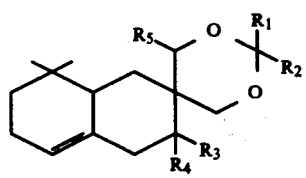

4. A compound of claim 1 having the basic formula

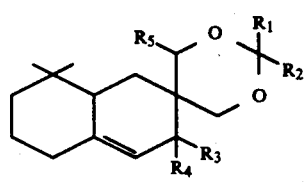

5. A compound of claim 1 having the basic formula

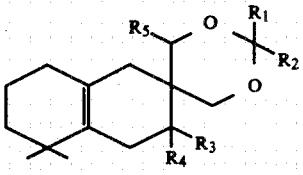

6. A compound of claim 1 having the basic formula

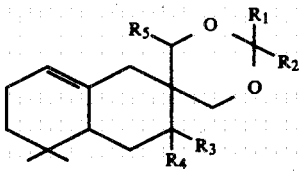

7. A compound of claim 1 having the basic formula

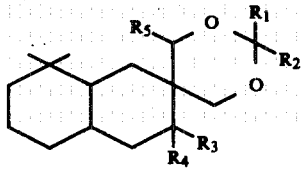

8. A compound of claim 1 having the basic formula

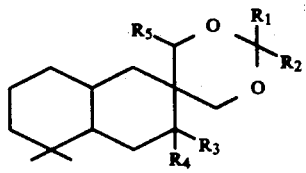

9. The compound of claim 1 having the basic formula

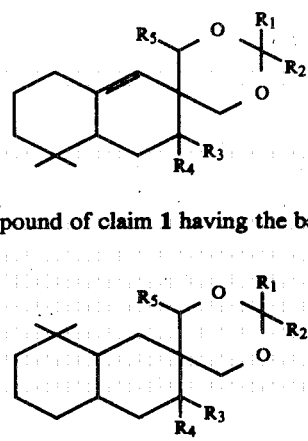

10. A mixture of two or more chemical compounds selected from the class consisting of compounds of claims 2, 3, 4, 5, 6 and 7 with identical substituents $R_1$, $R_2$, $R_3$, $R_4$ and $R_5$.

11. A mixture of two or more chemical compounds selected from the class consisting of compounds of the claims 2, 3 and 4 with identical substituents $R_1$, $R_2$, $R_3$, $R_4$ and $R_5$.

12. A mixture of two or more chemical compounds selected from the class consisting of compounds of the claims 5, 6 and 7 with identical substituents $R_1$, $R_2$, $R_3$, $R_4$ and $R_5$.

13. A mixture of two or more chemical compounds selected from the class consisting of compounds of the claims 8 and 9 with identical substituents $R_1$, $R_2$, $R_3$, $R_4$ and $R_5$.

14. A mixture of two or more chemical compounds selected from the class compounds having the basic structural formulae (a)    (b)

wherein the dotted lines represent the position of one carbon-to-carbon double bond.

15. A mixture of two or more chemical compounds selected from the class compounds having the basic structural formulae (a)    (b)

wherein the dotted lines represent the position of one carbon-to-carbon double bond.

16. A mixture of two or more chemical compounds selected from the class compounds having the basic structural formulae (a)    (b)

wherein the dotted lines represent the position of one carbon-to-carbon double bond.

17. A mixture of two or more chemical compounds selected from the class compounds having the basic structural formulae (a)    (b)

wherein the dotted lines represent the position of one carbon-to-carbon double bond.

18. A mixture of two or more chemical compounds selected from the class compounds having the basic structural formulae (a)    (b)

wherein the dotted lines represent the position of one carbon-to-carbon double bond.

19. A perfume composition containing, in combination with other olfactorily active ingredients, at least one compound according to claim 1 in the amount of 0.01% to about 50% by weight.

20. A perfume composition containing, in combination with other olfactorily active ingredients, at least one compound according to claim 2 in the amount of 0.01% to about 50% by weight.

21. A perfume composition containing, in combination with other olfactorily active ingredients, at least one compound according to claim 3 in the amount of 0.01% to about 50% by weight.

22. A perfume composition containing, in combination with other olfactorily active ingredients, at least one compound according to claim 4 in the amount of 0.01% to about 50% by weight.

23. A perfume composition containing, in combination with other olfactorily active ingredients, at least one compound according to claim 5 in the amount of 0.01% to about 50% by weight.

24. A perfume composition containing, in combination with other olfactorily active ingredients, at least one compound according to claim 6 in the amount of 0.01% to about 50% by weight.

25. A perfume composition containing, in combination with other olfactorily active ingredients, at least one compound according to claim 7 in the amount of 0.01% to about 50% by weight.

26. A perfume composition containing, in combination with other olfactorily active ingredients, at least one compound according to claim 8 in the amount of 0.01% to about 50% by weight.

27. A perfume composition containing, in combination with other olfactorily active ingredients, at least one compound according to claim 9 in the amount of 0.01% to about 50% by weight.

28. A perfume composition containing, in combination with other olfactorily active ingredients, the mixture of chemical compounds according to claim 10 in the amount of 0.01% to about 50% by weight.

29. A perfume composition containing, in combination with other olfactorily active ingredients, the mixture of chemical compounds according to claim 11 in the amount of 0.01% to about 50% by weight.

30. A perfume composition containing, in combination with other olfactorily active ingredients, the mixture of chemical compounds according to claim 12 in the amount of 0.01% to about 50% by weight.

31. A perfume composition containing, in combination with other olfactorily active ingredients, the mixture of chemical compounds according to claim 13 in the amount of 0.01% to about 50% by weight.

32. A perfume composition containing, in combination with other olfactorily active ingredients, the mixture of compounds according to claim 14 in the amount of 0.01% to about 50% by weight.

33. A perfume composition containing, in combination with other olfactorily active ingredients, the mixture of compounds according to claim 15 in the amount of 0.01% to about 50% by weight.

34. A perfume composition containing, in combination with other olfactorily active ingredients, the mixture of compounds according to claim 16 in the amount of 0.01% to about 50% by weight.

35. A perfume composition containing, in combination with other olfactorily active ingredients, the mixture of compounds according to claim 17 in the amount of 0.01% to about 50% by weight.

36. A perfume composition containing, in combination with other olfactorily active ingredients, the mixture of compounds according to claim 18 in the amount of 0.01% to about 50% by weight.

* * * * *